US012673172B2

(12) United States Patent
Meliniotis

(10) Patent No.: US 12,673,172 B2
(45) Date of Patent: Jul. 7, 2026

(54) UNIT DOSE DRY POWDER INHALER WITH BLISTER CAVITY INCLUDING A BOWL, CHANNEL AND TUBE

(71) Applicant: VECTURA DELIVERY DEVICES LIMITED, Wiltshire (GB)

(72) Inventor: Andreas Meliniotis, Cambridgeshire (GB)

(73) Assignee: VECTURA DELIVERY DEVICES LIMITED (GB)

( * ) Notice: Subject to any disclaimer, the term of this patent is extended or adjusted under 35 U.S.C. 154(b) by 672 days.

(21) Appl. No.: 18/020,530

(22) PCT Filed: Aug. 24, 2021

(86) PCT No.: PCT/EP2021/073418
§ 371 (c)(1),
(2) Date: Feb. 9, 2023

(87) PCT Pub. No.: WO2022/043336
PCT Pub. Date: Mar. 3, 2022

(65) Prior Publication Data
US 2023/0293831 A1 Sep. 21, 2023

(30) Foreign Application Priority Data

Aug. 25, 2020 (EP) ..................................... 20192645
May 7, 2021 (EP) ..................................... 21172658

(51) Int. Cl.
*A61M 15/00* (2006.01)
(52) U.S. Cl.
CPC .... *A61M 15/0043* (2014.02); *A61M 15/0003* (2014.02); *A61M 15/0046* (2014.02); *A61M 2202/064* (2013.01); *A61M 2207/10* (2013.01)

(58) Field of Classification Search
CPC .......... A61M 15/0003; A61M 15/0021; A61M 15/0043; A61M 15/0051; B65D 75/36; B65D 73/0057; B65D 73/0092
See application file for complete search history.

(56) References Cited

U.S. PATENT DOCUMENTS 4,150,744 A * 4/1979 Fennimore ................ A61J 1/16
206/439
5,042,472 A * 8/1991 Bunin ............... A61M 15/0043
D24/110.5

(Continued)

FOREIGN PATENT DOCUMENTS

CN 110709124 1/2020
DE 10 2014 017 409 A1 6/2016

(Continued)

OTHER PUBLICATIONS

International Search Report from corresponding International Application No. PCT/EP2021/03418, mailed Nov. 24, 2021.

*Primary Examiner* — Kathryn E Ditmer
(74) *Attorney, Agent, or Firm* — Davidson Kappel LLC

(57) ABSTRACT

The invention provides a unit dose dispenser in the form of a blister containing a dry powder for inhalation. The blister comprises a base material in which a cavity is formed comprising a bowl that contains the powder and a channel that opens into the bowl. The channel contains a tube that has separate sections that provide an air outlet and an air inlet. The air outlet is further from the bowl than the air inlet. The upper side of the tube is flat and level with the top of the channel A lid material, such as a foil or foil laminate, seals the cavity. The blister has a detachable portion which, when removed, exposes the air inlet and the air outlet. A process for making the unit dose dispensers is also provided, which (Continued)

is based on the conventional process for manufacturing blister strips for dry powder inhalers.

19 Claims, 9 Drawing Sheets

(56)                    References Cited

U.S. PATENT DOCUMENTS

| | | | |
|---|---|---|---|
| 5,797,392 | A | 8/1998 | Keldmann et al. |
| 6,401,712 | B1 * | 6/2002 | von Schuckmann ... A61J 1/035 |
| | | | 128/203.15 |
| 6,613,036 | B1 * | 9/2003 | Farmer .................... A61J 1/10 |
| | | | 604/408 |
| 6,722,363 | B1 * | 4/2004 | Von Schuckmann ....................... |
| | | | A61M 15/0023 |
| | | | 128/203.23 |
| 6,907,880 | B1 * | 6/2005 | Heckenmuller .. A61M 15/0036 |
| | | | 128/203.19 |
| 9,446,209 | B2 | 9/2016 | Richardson |
| 10,124,129 | B2 | 11/2018 | Dunne et al. |
| 11,110,233 | B2 | 9/2021 | Beller |
| 2007/0062548 | A1 * | 3/2007 | Horstmann ............. A24F 42/60 |
| | | | 131/270 |
| 2007/0181124 | A1 * | 8/2007 | Casper .................... A61P 35/00 |
| | | | 128/200.24 |
| 2008/0135441 | A1 * | 6/2008 | Meliniotis ......... A61M 15/0045 |
| | | | 53/133.8 |
| 2008/0190424 | A1 * | 8/2008 | Lucking ............ A61M 15/0043 |
| | | | 128/203.15 |
| 2008/0194023 | A1 | 8/2008 | Gerecht et al. |
| 2012/0002495 | A1 | 1/2012 | Cho et al. |
| 2012/0024905 | A1 | 2/2012 | Kneer |
| 2013/0291865 | A1 * | 11/2013 | Jones ................ A61M 15/0021 |
| | | | 128/203.15 |
| 2016/0220148 | A1 * | 8/2016 | Reisinger ................ A61B 5/097 |
| 2017/0119982 | A1 * | 5/2017 | Jones ................ A61M 15/0025 |
| 2017/0173282 | A1 * | 6/2017 | O'Sullivan ....... A61M 15/0018 |
| 2017/0312458 | A1 * | 11/2017 | Beller .............. A61M 15/0008 |
| 2018/0280639 | A1 * | 10/2018 | Alexander ........ A61M 15/0086 |
| 2019/0117917 | A1 | 4/2019 | Mattern |
| 2019/0358414 | A1 * | 11/2019 | Richardson ....... A61M 15/0091 |

FOREIGN PATENT DOCUMENTS

| | | | | |
|---|---|---|---|---|
| EP | 0 404 454 | A1 | 12/1990 | |
| EP | 3919107 | A1 * | 12/2021 | ........ A61M 16/0866 |
| FR | 2962344 | A1 * | 1/2012 | ........ A61M 15/0028 |
| JP | 2020515366 | | 5/2020 | |
| WO | WO 03/103563 | A2 | 12/2003 | |
| WO | WO 2005/037353 | A1 | 4/2005 | |
| WO | WO 2006/108876 | A2 | 10/2006 | |
| WO | WO-2007061621 | A2 * | 5/2007 | ............ B65D 83/04 |
| WO | WO 2010/086285 | A2 | 8/2010 | |
| WO | WO 2014/175815 | A1 | 10/2014 | |
| WO | WO2018/183528 | | 10/2018 | |
| WO | WO2018/187273 | | 10/2018 | |
| WO | WO 2019/008336 | A1 | 1/2019 | |

* cited by examiner

UNIT DOSE DRY POWDER INHALER WITH BLISTER CAVITY INCLUDING A BOWL, CHANNEL AND TUBE

TECHNICAL FIELD OF THE INVENTION

The present invention relates to an inhalation device for oral or nasal delivery of medicament in powdered form, more specifically to a unit dose inhaler which is formed as a blister that contains a dose of medicament for inhalation.

BACKGROUND TO THE INVENTION

It is common for dry powder formulations to be pre-packaged in individual doses, usually in the form of capsules or blisters. A blister is generally cold-formed from a ductile foil laminate and has a puncturable or peelable lid. The lid is usually heat-sealed around the periphery of the blister after the dose of powder has been placed into the blister.

Multi-dose inhalers, as disclosed in WO 2005/037353, contain a blister strip with number of doses to be used over a period of time, so that there is no need to insert a blister into the device each time it is used.

There are also unit-dose devices that receive only one blister at a time, for example WO 2010/086285. Once the dose contained in a blister has been inhaled, the blister is removed from the device and discarded by the patient. A new blister is then inserted for a subsequent dose. This avoids the need for a strip indexing mechanism and so greatly simplifies the construction and operation of the device. Nonetheless, the device must still have several components, such as a blister support, piercer and mouthpiece.

Disposable dosage forms that do not require a separate dispensing device are also known, for example from EP0404454 and DE102014017409. These require a specific production process to form and seal the air inlets and outlets.

Disposable dosage forms based on the conventional blister strip production process are also known. WO2014/175815 discloses an inhaler with a body comprising an air channel that contains a powder and a foil with inlet and outlet holes that are closed by a removable tape. WO2003/103563 discloses an inhaler with a body that contains powder, and in which an air inlet hole and an air outlet hole are formed, and a lidding material. The inlet and outlet may be opened by peeling off the lidding material or by breaking off portions of the body. However, in these inhalers, the air outlets are simply holes in the lid or body, so they are not a convenient shape for the user to inhale on.

US2013/0291865 discloses a dose delivery device which has a housing comprising a base and a lid that enclose a dose and a mouthpiece (e.g. a tube). The mouthpiece may be rotatable relative to the housing to form an opening in the housing. The mouthpiece is rotatably attached to the base or to the lid of the housing, or it may be rotatably attached to an additional component. Whilst this provides a dedicated mouthpiece, it requires an additional process step and/or an additional component to form the rotatable attachment. In another embodiment, the mouthpiece is slidably movable relative to the housing. This requires tabs on the mouthpiece to limit the movement of the mouthpiece relative to the base.

Thus there remains a need for a simple unit dose inhaler which is easy to use and inexpensive to produce.

BRIEF DESCRIPTION OF THE INVENTION

The present invention provides a very simple, low cost a unit-dose dry powder inhalation device which is easy to use and inexpensive to produce, because it is based on the conventional blister strip production process and has a tube on which the user inhales. Accordingly, in a first aspect, the present invention provides a unit dose dispenser in the form of a blister containing a dry powder for inhalation, wherein the blister comprises:

- a base material in which a cavity is formed, wherein the cavity comprises a bowl that contains the powder and a channel that opens into the bowl;
- a tube in the channel that has separate sections which provide an air outlet and an air inlet, wherein the air outlet is further from the bowl than the air inlet;
- a lid material, such as a foil or foil laminate, which seals the cavity;
- at least one detachable portion which, when removed, exposes the air inlet and the air outlet;

wherein the tube has a flat upper side which is level with the top of the channel.

The tube may have a semi-circular cross-section and the curved lower side may correspond in size and shape to the channel so that it is held in the channel by an interference fit.

The lid material may be bonded to the flat upper side of the tube.

The tube may be divided longitudinally into a central air outlet section and two air inlet sections, one on either side of the central section. The two air inlet sections may extend further into the bowl than the central outlet section. The extensions of the air inlet sections into the bowl may be shaped to match the inner surface of the bowl.

The unit dose dispenser may have a line of weakness, such as perforations, in the base material and/or the lid material between the detachable portion and the rest of the blister. The dispenser may have notches in one or both edges base material and/or the lid material between the detachable portion and the rest of the blister.

A pair of dispensers may be joined together so that the powders in both blisters can be inhaled simultaneously. A plurality of dispensers may be joined together in the form of a strip which provides a multi-day supply of powder, wherein each dispenser is detachable from the rest of the strip.

In a second aspect, the invention provides a process for producing unit dose dispensers according to the first aspect, the process comprising:

- forming cavities in a base material, each cavity comprising a bowl and a channel, that opens into the bowl;
- filling the powder into the bowls;
- placing a tube that has separate sections which provide the air outlet and the air inlet into the channel, wherein the air outlet is further from the bowl than the air inlet and wherein the tube has a flat upper side which is level with the top of the channel;
- sealing the cavities with a lid material; and, simultaneously or in either order:
- forming a detachable portion which, when removed, exposes the air inlet and the air outlet, and
- cutting the base and lid materials to form individual dispensers, or pairs of dispensers, or strips with a plurality of dispensers.

The detachable portion may be formed by creating a line of weakness, such as perforations or scores in the base material and/or the lid material. The detachable portion may additionally or alternatively be formed by creating notches in one or both edges of the base material and/or the lid material.

The process is adapted from the standard process for producing blister strips for dry powder inhalers. It can be implemented with mainly conventional materials and existing production equipment. It therefore provides a straightforward and inexpensive way of manufacturing simple unit dose dispensers.

DETAILED DESCRIPTION OF THE INVENTION

Figure 1:
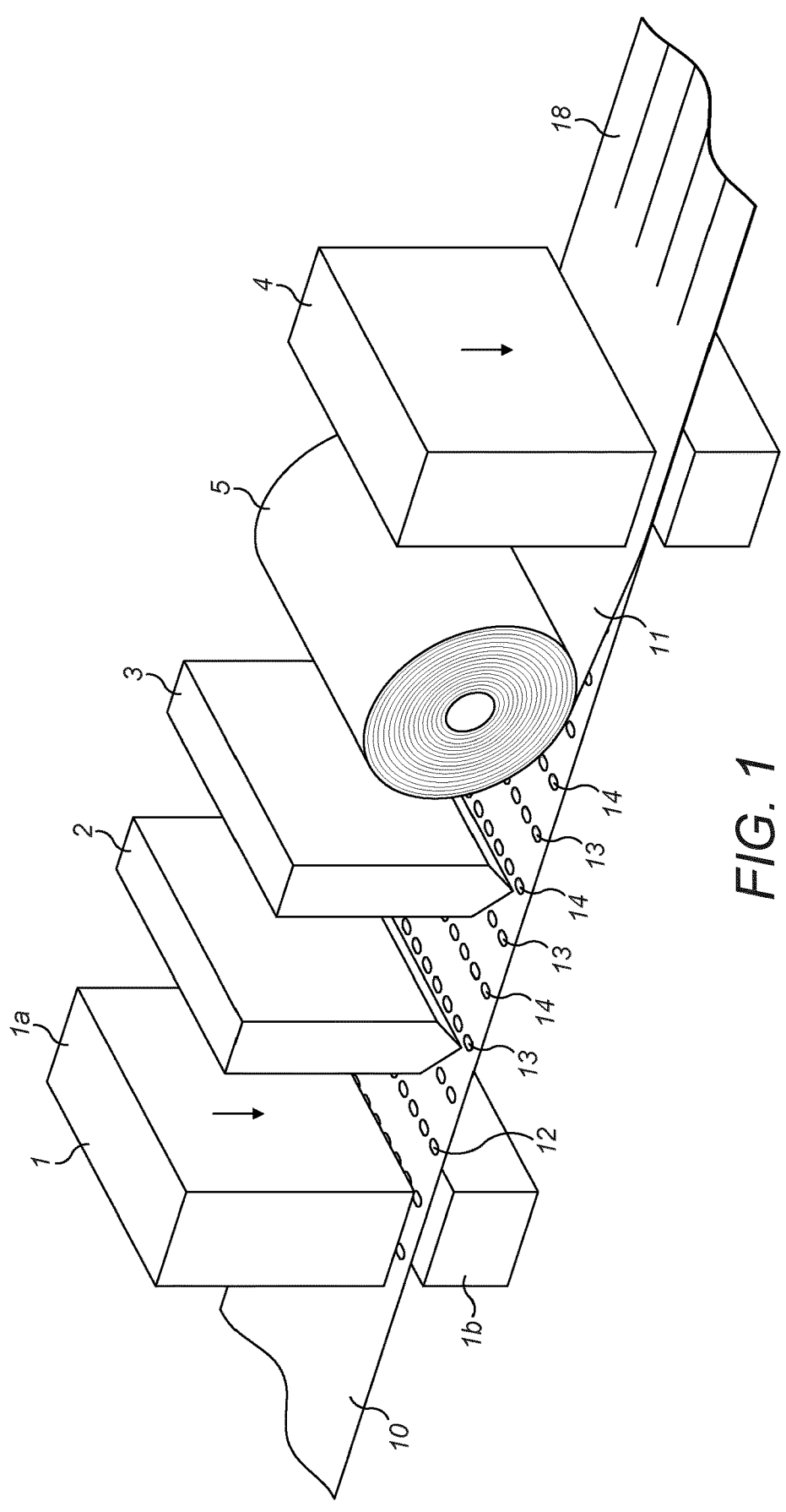
FIG. 1 shows a conventional process for producing blister strips for dry powder inhalers.

FIG. 1 shows a conventional process for producing blister strips for dry powder inhalers. The production line has a forming tool 1, two filling heads 2, 3 and a sealing tool 4. A sheet of base material 10 passes along the production line from left to right. A roll 5 of lid material 11 is located between the second filling head 3 and the sealing tool 4.

The base material is typically a laminate comprising a polymer layer in contact with the drug, a soft tempered aluminium foil layer and an external polymer layer, as described for example in WO 2006/108876. The aluminium provides a barrier to ingress of moisture, oxygen and light, whilst the polymer aids the adherence of the foil and provides a relatively inert layer in contact with the drug. Suitable materials for the polymer layer in contact with the drug include polyvinylchloride (PVC), polypropylene (PP) and polyethylene (PE). The polymer layer in contact with the drug is typically PVC of 30 µm thickness. However, a thicker or thinner layer of e.g. 60 µm or 15 µm may be used where a stiffer or more flexible laminate is required. Soft tempered aluminium is ductile so that it can be cold-formed into a blister shape. It is typically 45 µm thick. The external polymer layer provides additional strength and toughness to the laminate, and is typically made from oriented polyamide (oPA), typically 25 µm thick.

The lid material is typically a foil or a foil laminate preferably comprising a heat seal lacquer, a hard rolled aluminium layer and a top layer of primer, as described for example in WO 2006/108876. The heat seal lacquer bonds to the drug-contacting polymer layer of the base laminate during sealing to provide a seal around the top of the cavity. If the polymer layer in contact with the drug in the base material is PE, the heat seal lacquer on the lid material may be replaced with a further layer of PE. On heat-sealing, the two layers of PE melt and weld to each other. The aluminium layer is typically hard rolled and 20-30 µm thick. The primer facilitates printing onto the strip, for example dose numbers.

The sheet of base material 10 first passes through the forming station where it is cold formed to create rows of blister cavities 12 by moving the upper part 1a of the forming tool 1 downwards so that the base material is pressed between the upper 1a and the lower 1b parts. Then the formed base sheet passes under the filling stations 2, 3. Each filling station dispenses measured amounts of powder into a row of cavities. The two filling stations are spaced apart by an odd number of blister pitches (i.e. the distance between the centres of adjacent blister cavities in the longitudinal direction of the base sheet), and the base sheet is advanced by two blister pitches in each step. Thus the first filling station fills odd numbered rows 13 and the second filling station fills even numbered rows 14 of blister cavities. In practice, there may be a larger number of filling stations, for example six, in which case the base sheet advances by six blister pitches in each step. Next, the lid material 11 is dispensed from the roll 5 on top of the base sheet and the sealing tool 4 heats and compresses the base and lid material together in a region surrounding each cavity to form a heat-seal. Knives (not shown) cut the formed, filled and sealed blister sheet longitudinally into blister strips 18 as it advances, and also transversely to the required length.

Figure 2:
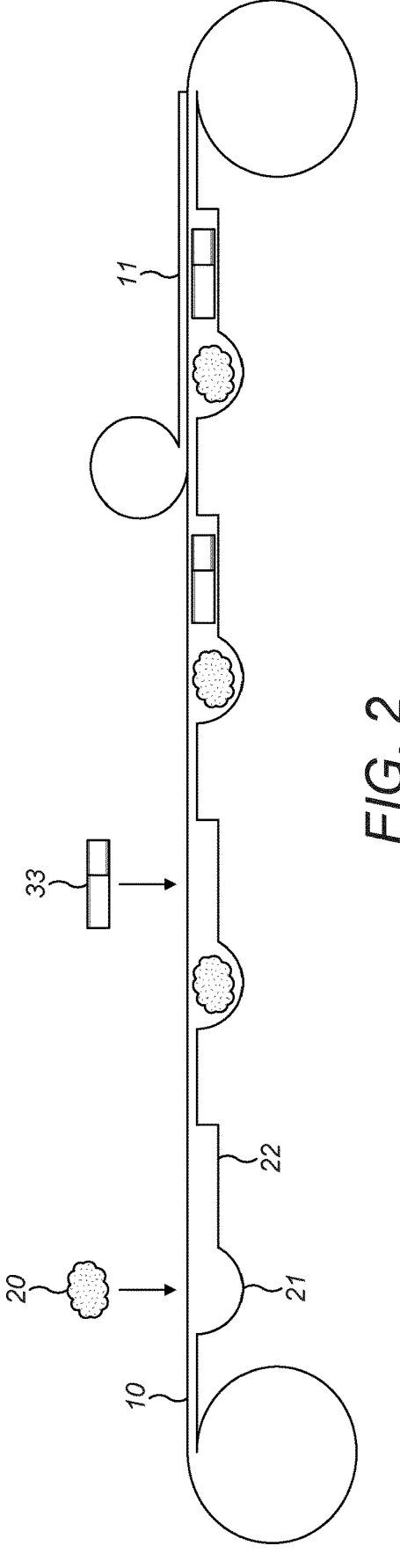
FIG. 2 shows the process of the invention.
Figure 3A:
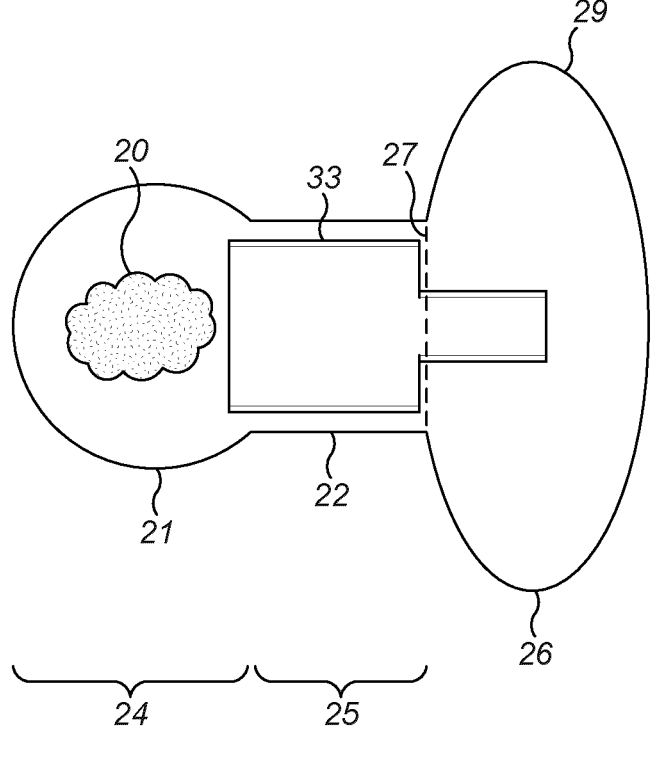
FIG. 3A shows a dispenser produced by the process of FIG. 2 before use.

FIG. 2 illustrates the process of the invention. The cavities are formed in the base sheet 10 in the same manner as the conventional process, but are shaped differently. As well as a bowl 21 into which the powder 20 is dispensed, the cavities also have a channel 22, one end of which opens into the bowl. A tube 33 is placed into the channel 22 from a magazine. Although FIG. 2 shows the tube 33 being placed into the channel 22 after the powder 20 has been filled into the bowl 21, these steps may occur simultaneously, or in either order. Placing the tube 33 into the channel 22 before the powder 20 is filled into the bowl 21 has the advantage that this avoids any possibility of powder being trapped underneath the tube. Then the cavities are sealed with lid material 11 in the same manner as the conventional process. The lid material may also bond to the top surface of the tube. Finally, the sheet is cut into individual dispensers, or strips of dispensers. The dispensers may be cut out to form a desired shape, for example with a detachable tab 26, as shown in FIG. 3A. A line of weakness 27, typically provided by perforations or scores in the lid and/or base material, and/or a notch in one or both edges may be formed between the tab and the remainder of the blister to facilitate removal of the tab. The position of the line of weakness may be indicated by a printed line on the on the lid material. Similarly, a line of weakness may be provided between each dispenser in a strip (as shown in FIG. 7), so that individual dispensers can be detached as needed.

Since the process is based on and adapted from the standard process for producing blister strips for dry powder inhalers, it can be implemented using mainly conventional materials and existing production equipment. It therefore provides a simple and inexpensive way of manufacturing unit dose dispensers.

Figure 3B:
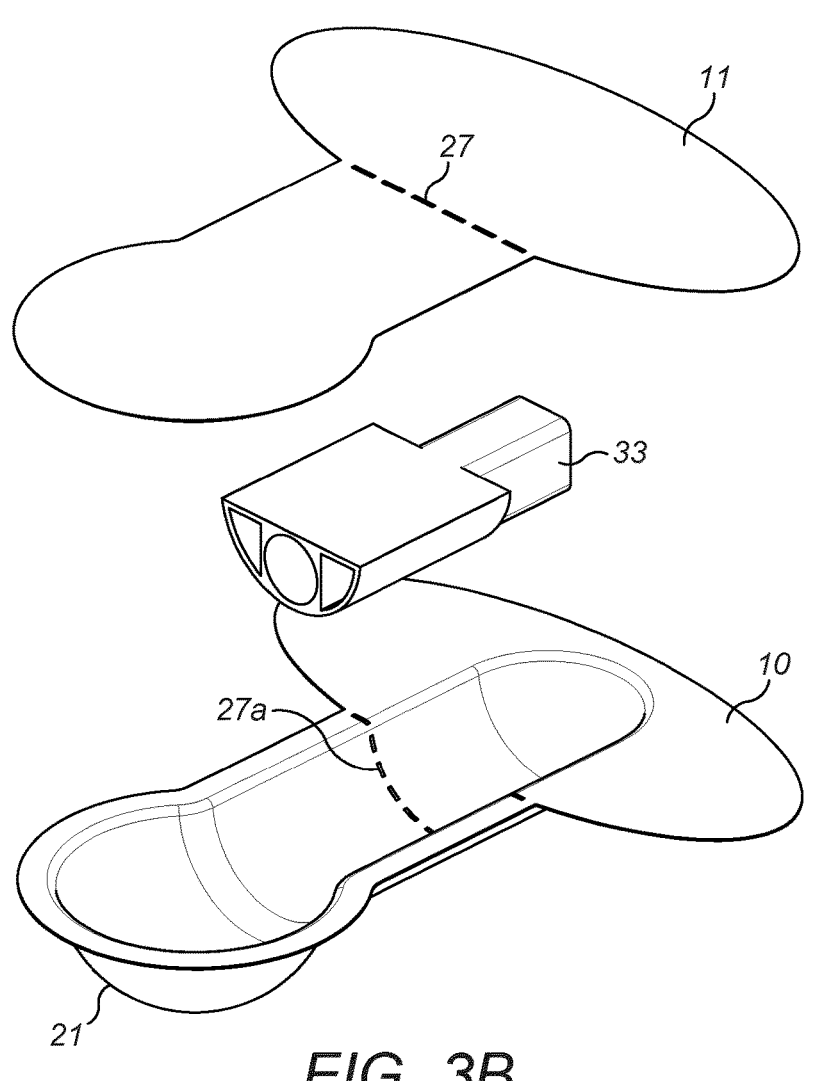
FIG. 3B is an expanded view.

FIGS. 3A-3E show the blister produced by the process of FIG. 2, after it has been cut out from the sheet to form an individual dispenser. FIG. 3A shows the blister from above, with the lid removed for illustration, so that the powder 20 and the tube 33 are visible in the bowl 21 and in the channel 22 respectively. FIG. 3B is an expanded view of the components of the blister, namely the base 10, tube 33 and lid 11 (but without the powder). The base of the blister has a main portion 24 in which the bowl 21 is formed, a neck 25 and a detachable portion, tab 26. The channel 22 extends from the bowl 21 along the neck 25 and into the detachable portion 26. A line of perforations 27 is formed in the lid between the neck 25 and the tab 26, and a corresponding line of perforations 27a is formed in the base.

Figure 3C:
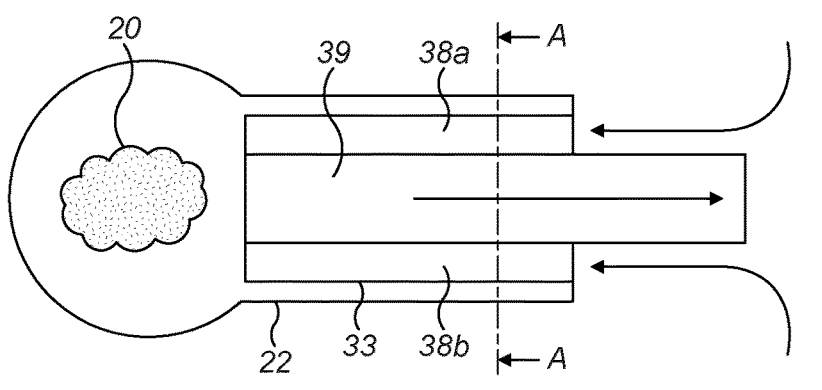
FIG. 3C shows the dispenser in use.

To prepare the blister for delivering a dose of medication, the user tears off the tab 26 to expose the tube 33, thereby exposing the air inlets and outlet. FIG. 3C shows the blister of FIG. 3A after the tab 26 has been torn off (with the lid removed for illustration, so that the powder 20 and the tube 33 are visible), and FIG. 3E is an isometric view. Since the channel 22 and tube 33 extend into the tab 26, the tube 33 protrudes beyond the neck 25 once the tab 26 has been removed. The blister is then ready to use. The tube is divided longitudinally into three sections, a central air outlet section 39 through which the user inhales and two air inlet sections 38a, 38b, one on either side.

Figure 3D:
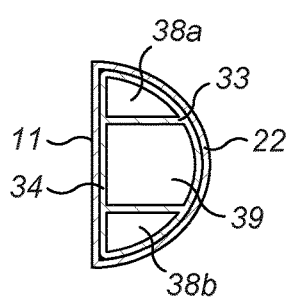
FIG. 3D shows a cutaway view along line A-A in FIG. 3C.
Figures 3E, 4:
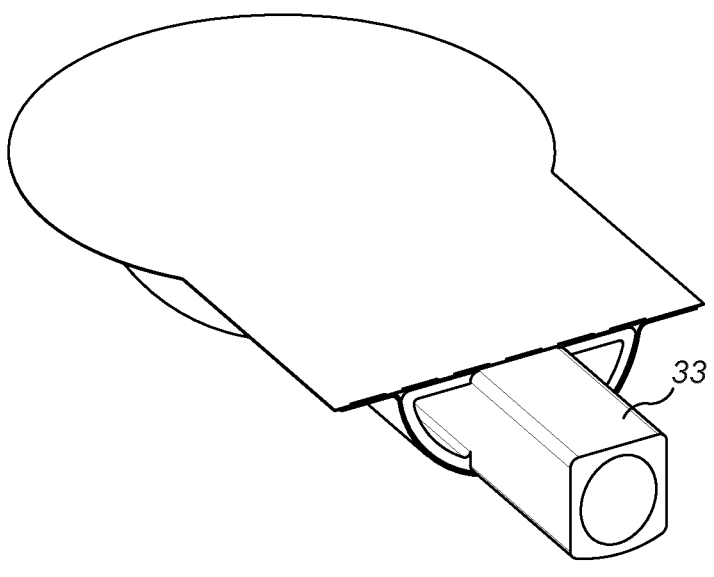
FIG. 3E is an isometric view.
FIG. 4 shows a variant of the dispenser of FIG. 3.

FIG. 3D shows a cutaway view along line A-A in FIG. 3C, but with the lid 11 in place. The flat upper side 34 of the tube 33 is adjacent to the lid 11. The curved lower side corresponds in size and shape to the channel 22 so that it is held in the channel 22 by an interference fit. Thus the tube 33 has a generally semi-circular cross-section.

The word "tube" as used herein does not refer to a tube with a circular cross-section and with a single passage. The tube according to the invention could have any shape with a flat upper side, for example a semi-circular cross-section and has two or more passages that provide air inlets/outlets, as illustrated in the embodiments described herein.

When the user inhales on the exposed end of the air outlet 39, air flows into the air inlets 38a, 38b (indicated by the arrows in FIG. 3C). The central outlet section 39 protrudes beyond the inlet sections 38a, 38b so that the user's lips do not block the air inlets 38a, 38b. The air enters the bowl 21, where it aerosolizes the powder 20. The aerosolized powder then flows out through the air outlet 39 and into the user's lungs.

The upper side of the tube 33 is flat and level with the top of the channel 32. This has the advantage that the lid foil can form a seal with the whole of the flat upper surface of the tube as well as the base, which helps to ensure that the tube is held securely in place. The tube may therefore have a heat seal lacquer on its upper side or be made from PE to facilitate formation of a heat seal with the lid, in the same manner as described above for the base material.

In a variant shown in FIG. 4, the air inlet sections 38a, 38b extend further into the bowl than the central outlet section 39, to ensure that the air flows through the centre of the bowl and aerosolizes the powder.

Figure 5A:
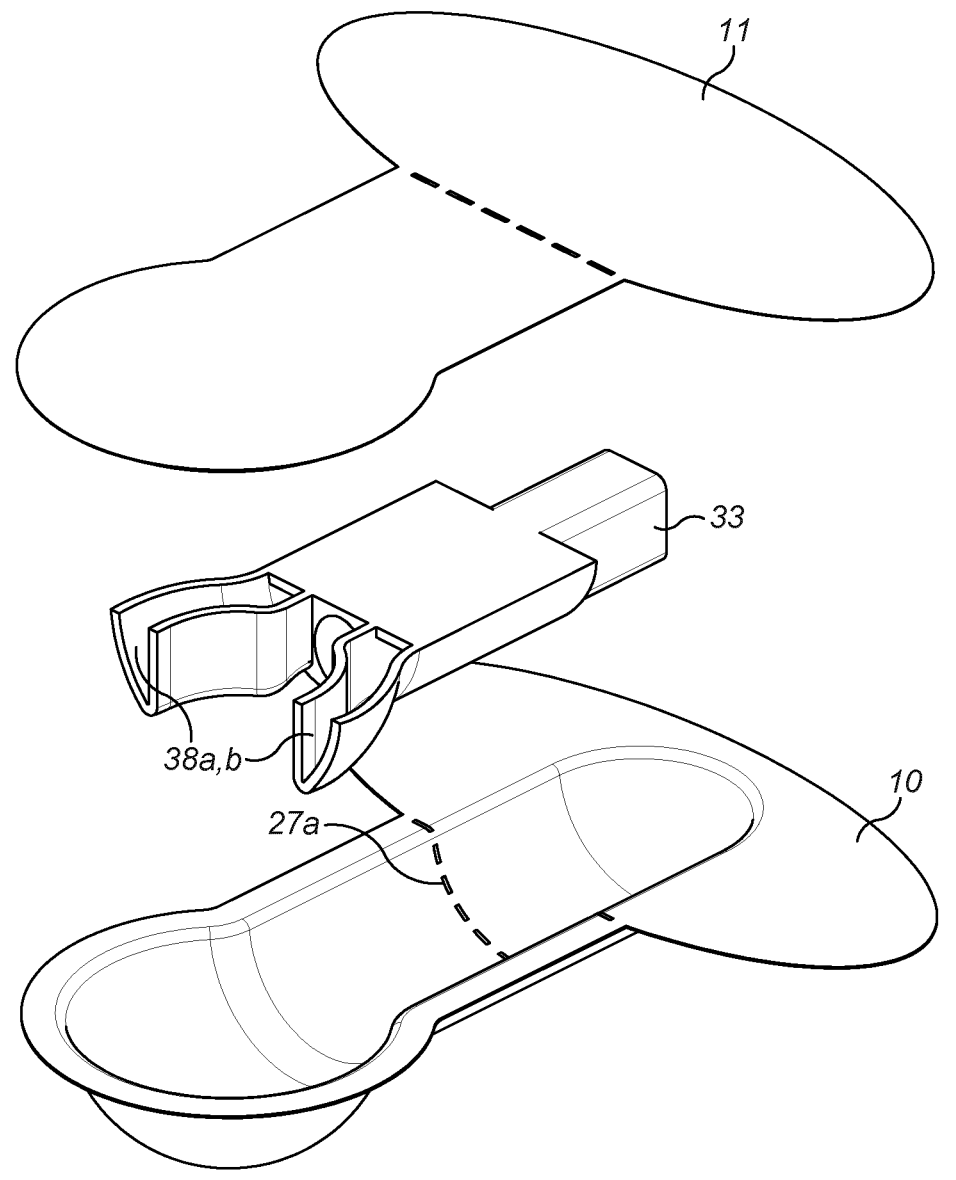
FIG. 5A is an expanded view showing a further variant.
Figure 5B:
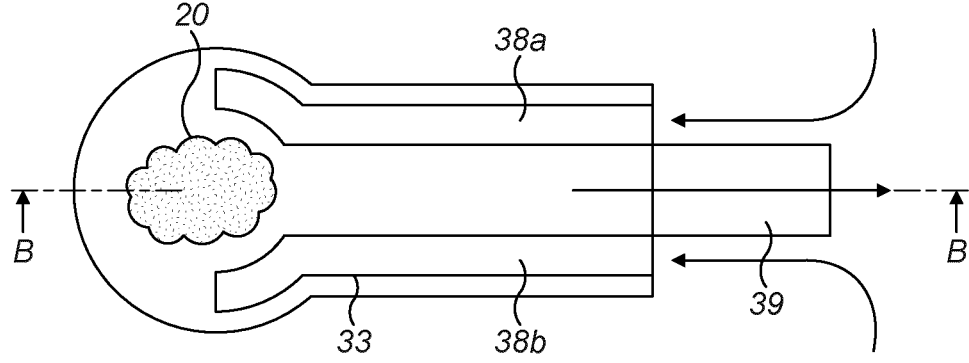
FIG. 5B shows the dispenser in use.
Figure 5C:
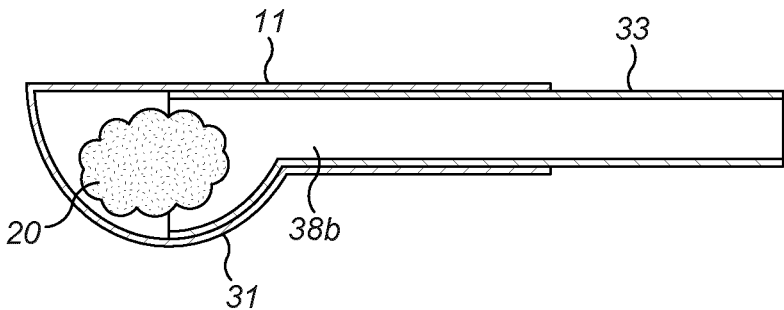
FIG. 5C is a cutaway view along line B-B in FIG. 5B.

FIG. 5 shows a variant of the embodiment of FIG. 4 in which the extensions of the air inlet sections 38a, 38b are curved so that they match the inner surface of the bowl. FIG. 5A is an expanded view of the base 10, tube 33 and lid 11 (but without the powder). FIG. 5B shows the blister once the tab has been detached, with the lid removed for illustration, so that the powder 20 and the tube 33 are visible. FIG. 5C shows a cutaway view along line B-B of FIG. 5A, but with the lid 11 in place. The shaped extensions of the air inlet sections 38a, 38b help to hold the tube in place so that it cannot be pulled out along the channel.

Figures 6A, 6B:
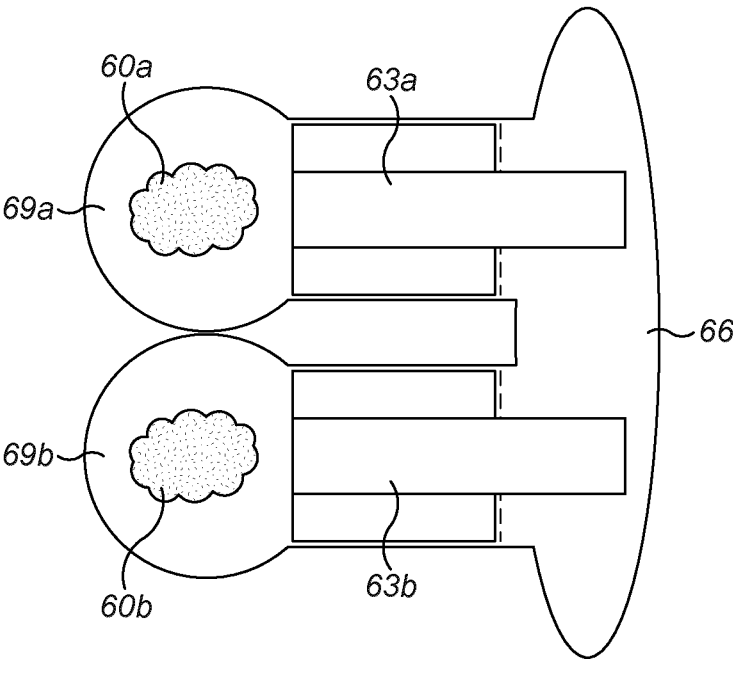
FIG. 6A shows a pair of dispensers for simultaneous administration.
FIG. 6B is a cutaway side view when the dispensers are folded so as to lie one on top of the other.

FIG. 6 shows an embodiment which is designed to deliver the contents of two blisters simultaneously, for example in order to deliver a double dose, or to deliver two different medicaments simultaneously, for example if the two medicaments cannot be stored together in a single blister. FIG. 6A shows two blisters 69a, 69b of the type shown in FIG. 3 joined together. However, they could be any of the types of blister described above. The blisters are shown with the lid removed for illustration, so that the powders 60a, 60b are visible. The blisters are cut out as a joined pair, rather than individual blisters. The user tears off the tab 66, thereby exposing two tubes 63a, 63b. The tubes are close enough together that the user can put both of them between their lips and inhale. The blisters 69a, 69b could also be folded, for example, after the tab has been removed, so that one lies on top of the other (i.e. with the lids 11 touching each other). The tubes 63a, 63b are thereby arranged one above the other, as shown in the cutaway side view of FIG. 6B.

Figures 7A, 7B:
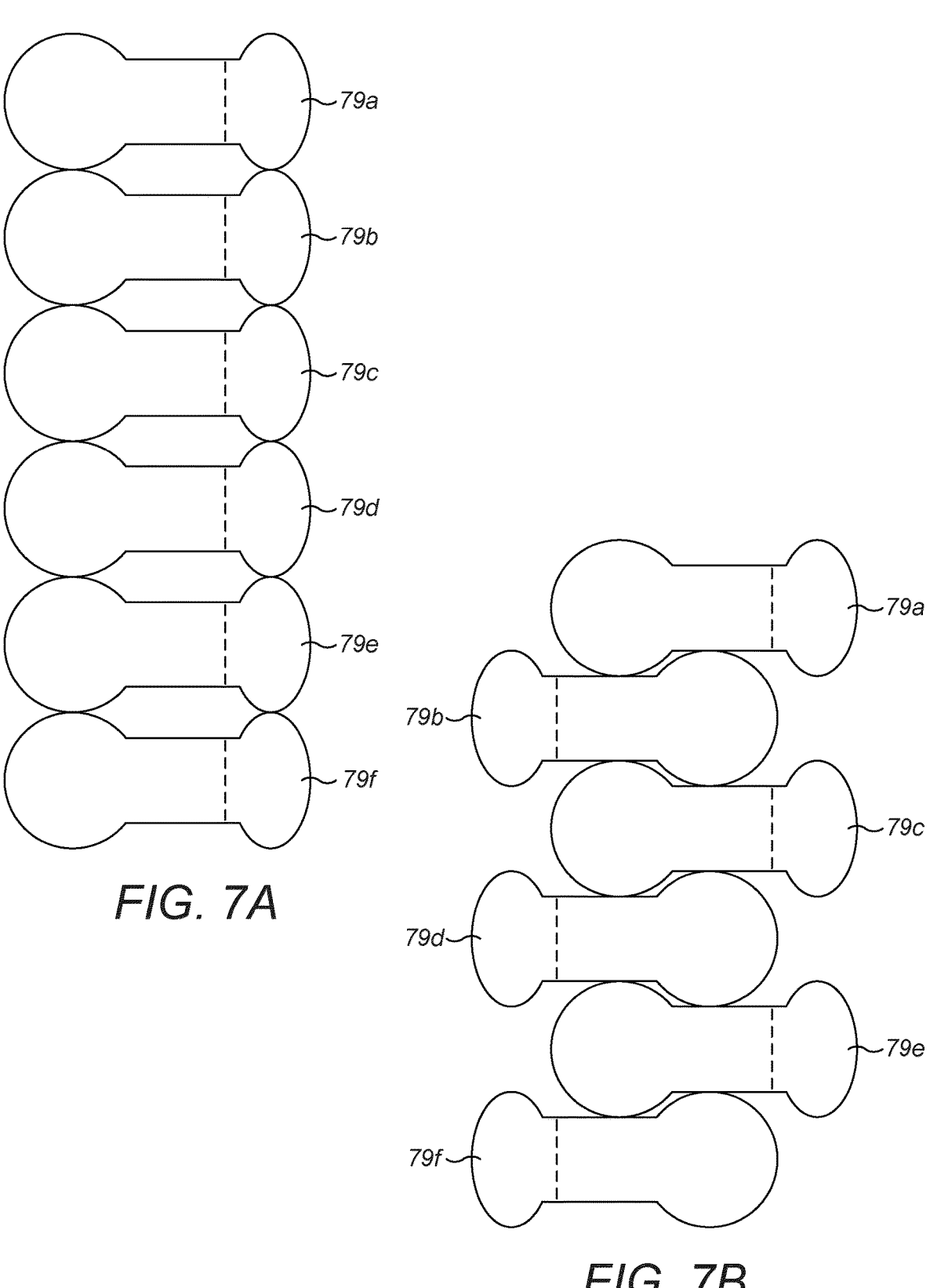
FIG. 7 shows strips of six dispensers.

The dispensers may be provided as a strip of several (e.g. six or ten) blisters 79a-f, shown in FIG. 7. In FIG. 7A, the blisters are all oriented in the same direction; in FIG. 7B, adjacent blisters are oriented in opposite directions. Since in the embodiments shown the main portion of the blister is wider than the neck portion, this alternating arrangement allows for closer packing. Each dispenser is detachable from the rest of the strip, for example by a line of perforations, so that individual dispensers can be detached as needed. A number of strips of dispensers may be provided in a pack, for example 30 days' supply of drug in the form of five strips with six dispensers per strip.

The invention provides a very simple unit dose dry powder inhaler. It can be manufactured using the existing process for producing blisters, and requires only one simple additional component (the tube), so it is inexpensive and easy to produce.

The medicament is suitable for administration by inhalation, for example for the treatment of a respiratory disease. It may include one or more of the following classes of pharmaceutically active material: anticholinergics, adenosine A2A receptor agonists, β2-agonists, calcium blockers, IL-13 inhibitors, phosphodiesterase-4-inhibitors, kinase inhibitors, steroids, CXCR2, proteins, peptides, immunoglobulins such as Anti-IG-E, nucleic acids in particular DNA and RNA, monoclonal antibodies, small molecule inhibitors and leukotriene B4 antagonists. The medicament may include excipients, such as fine excipients and/or carrier particles (for example lactose), and/or additives (such as magnesium stearate, phospholipid or leucine).

Suitable β2-agonists include albuterol (salbutamol), preferably albuterol sulfate; carmoterol, preferably carmoterol hydrochloride; fenoterol; formoterol; milveterol, preferably milveterol hydrochloride; metaproterenol, preferably metaproterenol sulfate; olodaterol; procaterol; salmeterol, preferably salmeterol xinafoate; terbutaline, preferably terbutaline sulphate; vilanterol, preferably vilanterol trifenatate; or indacaterol, preferably indacaterol maleate.

Suitable steroids include budesonide; beclamethasone, preferably beclomethasone dipropionate; ciclesonide; fluticasone, preferably fluticasone furoate; or mometasone, preferably mometasone furoate.

Suitable anticholinergics include: aclidinium, preferably aclidinium bromide; glycopyrronium, preferably glycopyrronium bromide; ipratropium, preferably ipratropium bromide; oxitropium, preferably oxitropium bromide; tiotropium, preferably tiotropium bromide; umeclidinium, preferably umeclidinium bromide; Darotropium bromide; or tarafenacin.

The active material may include double or triple combinations such as salmeterol xinafoate and fluticasone propionate; budesonide and formoterol fumarate dehydrate; glycopyrrolate and indacaterol maleate; glycopyrrolate, indacaterol maleate and mometasone furoate; fluticasone furoate and vilanterol; vilanterol and umeclidinium bromide; fluticasone furoate, vilanterol and umeclidinium bromide.

The invention claimed is:

1. A unit dose dispenser in the form of a blister containing a dry powder for inhalation, wherein the blister comprises:
   a base material in which a cavity is formed, wherein the cavity comprises a bowl that contains the powder and a channel that opens into the bowl;

a lid material which seals the cavity; and at least one detachable portion which, when removed from the remainder of the blister, exposes an air inlet to the bowl and an air outlet from the bowl via the channel;

wherein the channel contains a tube that has separate sections which provide the air outlet and the air inlet, and the air outlet is farther from the bowl than the air inlet, wherein the tube has a flat upper side which is level with a top of the channel and wherein the tube is divided longitudinally into a central air outlet section and two air inlet sections, one on either side of the central section, wherein the two air inlet sections comprise extensions that extend farther into the bowl than the central outlet section.

2. The unit dose dispenser according to claim 1, wherein the tube has a semi-circular cross-section and a curved lower side corresponds in size and shape to the channel so that it is held in the channel by an interference fit.

3. The unit dose dispenser according to claim 1, wherein the lid material is bonded to the flat upper side of the tube.

4. The unit dose dispenser according to claim 1, wherein the extensions of the air inlet sections into the bowl are shaped to match an inner surface of the bowl.

5. The unit dose dispenser according to claim 1, which has a line of weakness between the at least one detachable portion and the rest of the blister, wherein the location of the line of weakness is selected from the group consisting of the base material, the lid material, and combinations thereof.

6. The unit dose dispenser according to claim 5, wherein the line of weakness is comprised of perforations.

7. The unit dose dispenser according to claim 5, wherein the line of weakness is comprised of scores.

8. The unit dose dispenser according to claim 5, which has an at least one notch between the at least one detachable portion and the rest of the blister, wherein the location of the at least one notch is selected from the group consisting of a first edge of the base material, the first edge of the base material and a second edge of the base material, a first edge of the lid material, the first edge of the lid material and a second edge of the lid material and combinations thereof.

9. The unit dose dispenser according to claim 1, which has an at least one notch between the at least one detachable portion and the rest of the blister, wherein the location of the at least one notch is selected from the group consisting of a first edge of the base material, the first edge of the base material and a second edge of the base material, a first edge of the lid material, the first edge of the lid material and a second edge of the lid material and combinations thereof.

10. The unit dose dispenser in the form of a blister containing a dry powder for inhalation of claim 1, wherein the lid material is a foil or foil laminate.

11. A pair of dispensers according to claim 1, which are joined together so that the powders in both blisters can be inhaled simultaneously.

12. A strip comprising a plurality of dispensers according to claim 1, which provide a multi-day supply of powder, wherein each dispenser is detachable from the rest of the strip.

13. A process for producing unit dose dispensers according to claim 1, the process comprising:

forming cavities in a base material, each cavity comprising a bowl, and a channel that opens into the respective bowl;

filling a powder into the respective bowl;

placing a tube that has separate sections which provide an air outlet and an air inlet into each channel, wherein each air outlet is farther from the respective bowl than each air inlet and wherein each tube has a flat upper side which is level with the top of the respective channel and further wherein each tube is divided longitudinally into a central air outlet section and two air inlet sections, one on either side of the central section, wherein the two air inlet sections comprise extensions that extend farther into the bowl than the central outlet section;

sealing each cavity with a lid material; and, simultaneously or in either order:

forming at least one detachable portion which, when removed from the remainder of an associated unit dose dispenser, exposes an associated air inlet and an associated air outlet;

cutting the base and lid materials to form individual dispensers, or pairs of dispensers, or strips with a plurality of dispensers.

14. The process according to claim 13, wherein the at least one detachable portion is formed by creating a line of weakness, wherein the location of the line of weakness is selected from the group consisting of the base material, the lid material, and combinations thereof.

15. The process according to claim 14, wherein the line of weakness is comprised of perforations.

16. The process according to claim 14, wherein the line of weakness is comprised of scores.

17. The process according to claim 14, wherein the at least one detachable portion is formed by creating an at least one notch between the at least one detachable portion and the rest of an associated unit dose dispenser, wherein the location of the at least one notch is selected from the group consisting of a first edge of the base material, the first edge of the base material and a second edge of the base material, a first edge of the lid material, the first edge of the lid material and a second edge of the lid material and combinations thereof.

18. The process according to claim 13, wherein the at least one detachable portion is formed by creating an at least one notch between the at least one detachable portion and the rest of an associated unit dose dispenser, wherein the location of the at least one notch is selected from the group consisting of a first edge of the base material, the first edge of the base material and a second edge of the base material, a first edge of the lid material, the first edge of the lid material and a second edge of the lid material and combinations thereof.

19. The process according to claim 13, further comprising bonding the lid material to the flat upper side of each tube.

* * * * *